United States Patent
Philippe

(10) Patent No.: US 6,371,147 B1
(45) Date of Patent: Apr. 16, 2002

(54) EVALUATION AND REGULATION OF THE THERMAL POWER OF A FLOW OF COMBUSTIBLE GAS; CHARACTERIZATION OF A THERMAL MASS FLOWMETER

(75) Inventor: Louis Philippe, Toussus le Noble (FR)

(73) Assignee: L'Air Liquide, Societe Anonyme pour l'etude et l'Exploitation des Procedes Georges Claude, Paris, Cedex (FR)

( * ) Notice: Subject to any disclaimer, the term of this patent is extended or adjusted under 35 U.S.C. 154(b) by 0 days.

(21) Appl. No.: 09/545,000

(22) Filed: Apr. 6, 2000

(30) Foreign Application Priority Data

Apr. 15, 1999 (FR) .............................................. 9904748

(51) Int. Cl.[7] .................................................. E03B 1/00
(52) U.S. Cl. ........................... 137/6; 137/9; 137/487.5; 374/36; 73/23.31; 73/198
(58) Field of Search ............................ 73/23.31, 23.32, 73/204.11, 198; 137/6, 9, 101.21, 114, 487.5; 374/36, 37

(56) References Cited

U.S. PATENT DOCUMENTS

| | | | | |
|---|---|---|---|---|
| 2,072,384 A | * | 3/1937 | Schmidt | ........................ 137/6 |
| 4,384,792 A | * | 5/1983 | Sommers et al. | ............... 374/6 |
| 4,745,941 A | * | 5/1988 | Nilsson | ....................... 137/114 |

FOREIGN PATENT DOCUMENTS

| | | |
|---|---|---|
| EP | 0 323 658 | 7/1989 |
| EP | 0 560 501 | 9/1993 |
| GB | 2 296 091 | 6/1996 |

* cited by examiner

Primary Examiner—Michael Powell Buiz
Assistant Examiner—Ramesh Krishnamurthy
(74) Attorney, Agent, or Firm—Burns, Doane, Swecker & Mathis, L.L.P.

(57) ABSTRACT

The subject of the present invention is:
- processes for the evaluation and the regulation, to a value $P_0$, of the net (or gross) thermal power P of a flow of a combustible gas CG of composition close to that of a reference gas, said flow of gas passing through a flowmeter (7) of thermal mass technology, which is standardized, or standardized and calibrated, for said reference gas;
- a method of characterizing a flowmeter of thermal mass technology.

19 Claims, 2 Drawing Sheets

EVALUATION AND REGULATION OF THE THERMAL POWER OF A FLOW OF COMBUSTIBLE GAS; CHARACTERIZATION OF A THERMAL MASS FLOWMETER

BACKGROUND OF THE INVENTION

1. Field of the Invention

The present invention relates to:

a process and a device for the evaluation of the thermal (or calorific) power of a flow of a combustible gas;

a process and a device for the regulation of the thermal (or calorific) power of a flow of a combustible gas;

a method of characterizing a flowmeter of thermal mass technology.

2. Description of the Related Art

Hot-wire mass flowmeters are well known for industrial or laboratory usage. Their property of offering a wide measurement range makes them particularly attractive: they can be used in measurement ranges varying from 1 to 100. These flowmeters indicate, in a manner known per se, mass or volume flow rates under standard temperature and pressure conditions. This is because their operating principle is based on the measurement of a temperature difference ($\Delta\theta$), proportional to the product of the heat capacity (Cp) of the gas, the density ($\rho$) of said gas and the volume flow rate ($\phi_v$) of said gas, under standard temperature and pressure conditions:

$$\Delta\theta = kCp\rho\phi_v$$
$$= kCp\phi_m \quad (\phi_m: \text{mass flow rate of said gas}).$$

The use of hot-wire mass flowmeters for measuring gas volume flow rates requires knowledge of, among other things, the density $\rho$ of the gas and the heat capacity Cp of the gas in question. Before it is used, a mass flowmeter must therefore be standardized for the gas whose flow rates will be measured. To measure the flow rate of a second gas, it is necessary to multiply the flow rate indicated by the mass flowmeter by a correction factor F. If the composition of the second gas is close to that of the gas for which the flowmeter has been standardized, the correction factor F may be approximated by $\rho_1 Cp_1$ divided by $\rho_2 Cp_2$, the index 1 corresponding to the gas for which the flowmeter was standardized and the index 2 corresponding to the second gas for which the flow rate is measured. Thus, in order for a flowmeter to deliver an accurate value of flow rate for a given gas, it is necessary either to standardize it using this gas or to calibrate it by applying a correction factor to the measurement.

In the case of natural gas, this problem is difficult to solve since the chemical composition of the gas varies depending on the location of the point of use and on the source of supply, said source of supply possibly varying over time. The inaccuracies in the volume flow rate measurement may exceed 10% for a flowmeter standardized for pure methane, used with natural gas.

For an industrialist using such a gas as combustible gas, the variations in the chemical composition of said gas are sources of problems since the changes in chemical composition are manifested by changes in calorific power. It is therefore difficult to evaluate and regulate, very accurately, a thermal power (the volume flow rate measured under standard temperature and pressure conditions multiplied by the (net or gross) calorific value) of a flow of gas based on knowing a flow rate given by a mass flowmeter.

SUMMARY OF THE INVENTION

The object of the invention is to solve this difficulty by proposing judicious processes and devices making it possible, respectively, to evaluate and regulate the thermal power of a flow of a combustible gas.

The process and devices of the present invention are for the evaluation and the regulation, to a value $P_0$, of the net (or gross) thermal power P of a flow of a combustible gas similar in composition to that of a reference gas, with the flow of gas passing through a flowmeter of thermal mass technology, which is standardized, or standardized and calibrated, for the reference gas. In another embodiment, there is provided a method for calibrating a flowmeter of thermal mass technology.

$$F_{NG/CH_4}(NCV_{NG}/NCV_{CH_4})$$

for a natural gas as a function of the Wobbe index of said natural gas.

Figure 2:
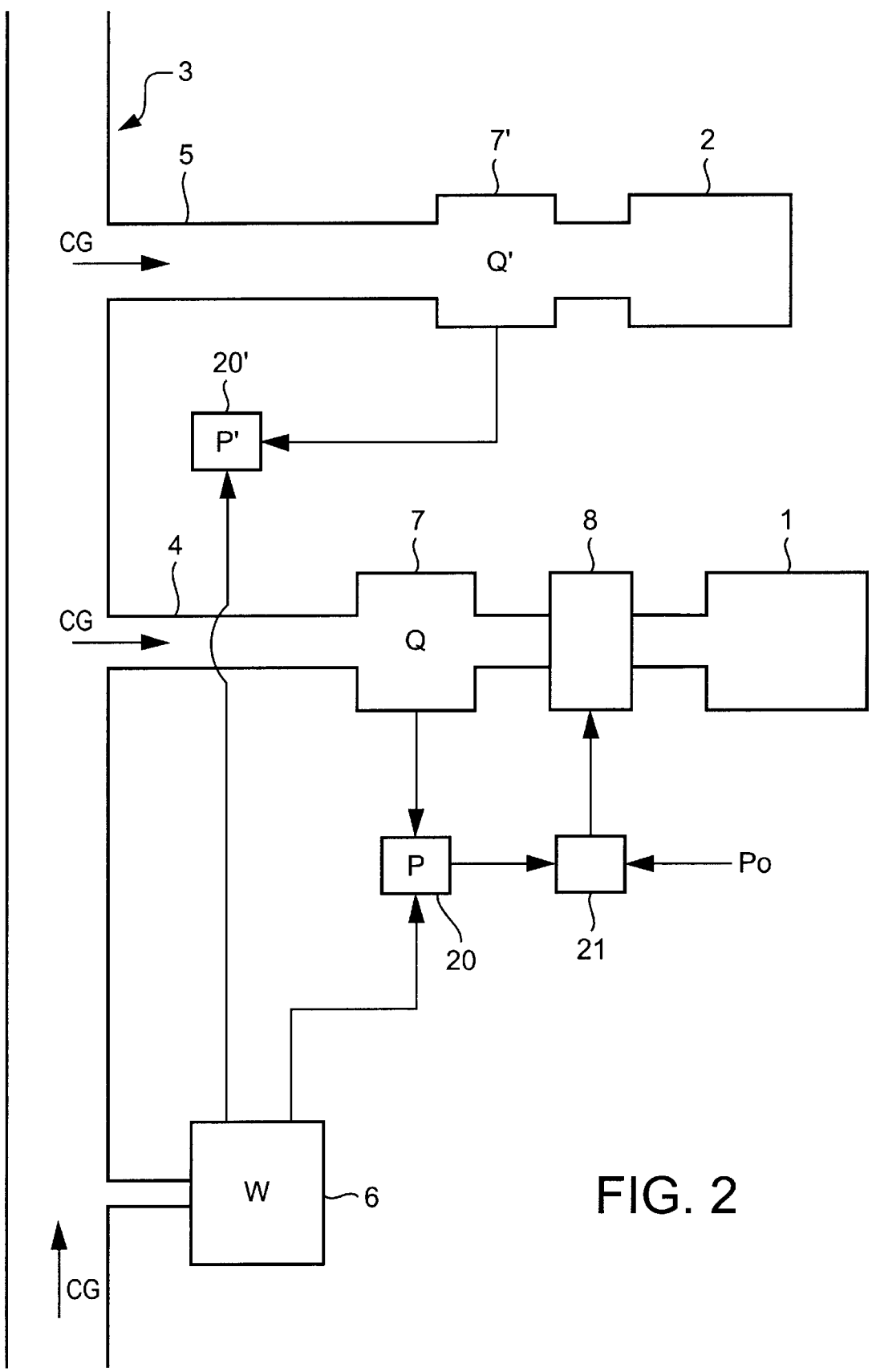

FIG. 2 of the Drawing schematically depicts a distribution system for a combustible gas suitable for the processes of the present invention.

DETAILED DESCRIPTION OF THE PREFERRED EMBODIMENTS

More specifically, the invention proposes a process for the evaluation of the net (or gross) thermal power P of a flow of a combustible gas of composition close to that of a reference gas (consequently itself a combustible gas), said flow of gas passing through a flowmeter of thermal mass technology which is standardized, or standardized and calibrated, for said reference gas, comprising:

a step of collecting the information given by said flowmeter;

a step of determining the Wobbe index of the gas; and a step of calculating said net (or gross) thermal power P by multiplying the collected information by the net (or gross) calorific value of said reference gas and by an essentially affine function of the Wobbe index of the gas.

A person skilled in the art will know that there are two contexts for implementing the process of the invention specified above:

context a: the flowmeter used has been standardized for the reference gas (standard gas=said reference gas), then the measurement, read on said flowmeter during the flow of said reference gas, corresponds to the actual flow rate;

context b: the flowmeter used has been standardized for a gas different from the reference gas (standard gas≠said reference gas), then the measurement, read on said flowmeter during flow of said reference gas, must be corrected in order to correspond to the actual flow rate of reference gas. The correction factor ($F_{ref/stand}$) may be approximated by the ratio of the $\rho Cps$ $$\left(F_{ref/stand} = \frac{\rho_{stand} Cp_{stand}}{\rho_{ref} CP_{ref}}\right).$$

After these standardizing, or standardizing and calibrating, steps, the flowmeter involved gives an accurate flow rate measurement when the reference gas flows through it.

The invention also proposes a process for the regulation of the net (or gross) thermal power P of a flow of a combustible gas of composition close to that of a reference gas (consequently itself a combustible gas) to a value $P_0$, said flow of gas passing through a flowmeter of thermal mass technology which is standardized, or even standardized and calibrated, for said reference gas, comprising:

the evaluation of said net (or gross) thermal power P, according to the process specified above;

the regulation of said power P (using regulating methods known per se) to said value $P_0$.

The above regulation may obviously be used equally well in both contexts a and b specified above.

It may be used in various different ways. In particular, it is possible to regulate the flow rate of the combustible gas involved or the composition of said gas.

The above processes rely on the discovery by the inventor of a simple correlation between the Wobbe index (W) and the ratio of the actual net thermal power at a burner (P) to the apparent power (Pc) calculated by multiplying the apparent volume flow rate, given by a mass flowmeter standardized, or standardized and calibrated, for the reference gas, by the net calorific value of said reference gas, which affine correlation is written as:

$$\frac{P}{Pc} = f(W) = aW + b$$

Figure 1:
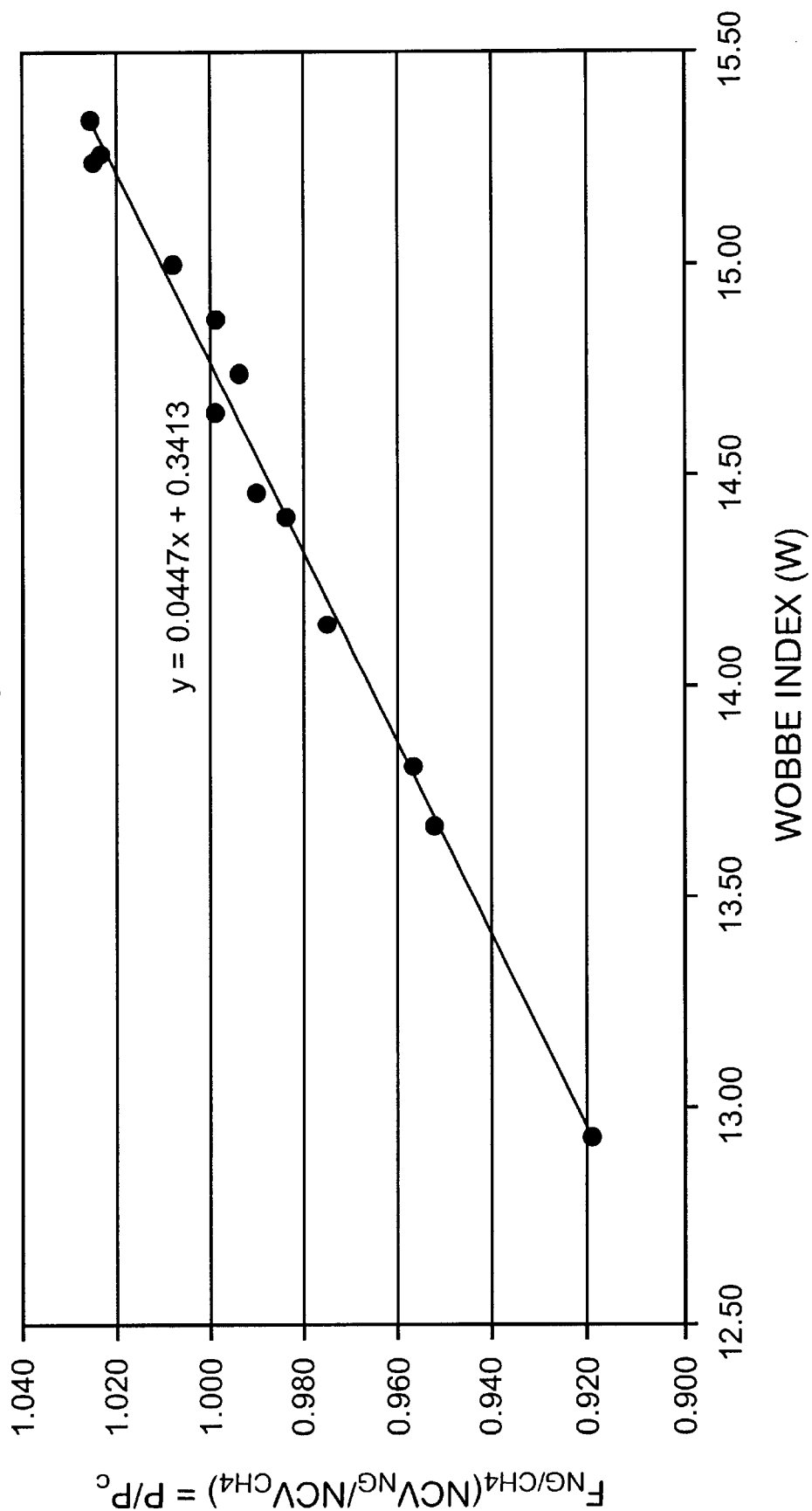
FIG. 1 of the Drawing graphically represents the product.

(see the appended FIG. 1).

The correlation is referred to in the present text as being an "essentially" affine function but it is not at all excluded, within the scope of the invention, to refine the above correlation by adding at least one quadrative term to it. More than satisfactory accuracy is in any case obtained using a function of the first degree.

The coefficients used in said correlation (coefficients characterizing the flowmeter) obviously depend on the nature of the combustible reference gas.

Insofar as, in order for the combustion of the gas to be used, an oxidizer gas is generally employed, the evaluation and regulation processes as defined above advantageously also include a step of regulating the flow rate of oxidizer employed to the value $Q_0'$ equal to $(1+x)P/K$, where x is the excess oxidizer (x being expressed as a percentage with respect to the flow rate of oxidizer needed for stoichiometric combustion of the gas and where K is a constant which depends on the oxidizer.

It should be understood that, when it is the net thermal power of the gas that is of interest, the net calorific value of the reference gas is used and that, when it is the gross power of said gas that is of interest, the gross calorific value of said reference gas is used.

Advantageously, said reference gas is:

pure methane or a reference natural gas, when the combustible gas in question is a natural gas;

pure propane or a reference propane, when the combustible gas in question is industrial propane;

pure butane or a reference butane, when the combustible gas in question is industrial butane.

In the context of an advantageous way of implementing the processes of the invention, the combustible gas used is a natural gas, the reference gas is methane and the essential affine function is written as:

$$f(W)=aW+b,$$

a being between 0.035 and 0.050 and b being between 0.30 and 0.45. The coefficients a and b may in fact vary slightly according to the way of carrying out the method of characterizing the flowmeter, as described below.

It is possible for the Wobbe index of the gas used to be determined in several ways. In particular, it is possible to place, on the supply main for said gas, "an analyzer" which measures physical parameters of said gas (such as its gross calorific value, its relative density with respect to air, its chemical composition, its oxidizability index, etc.) from which the Wobbe index is calculated. Such an analyzer may consist of a combustibility analyzer which measures the combustibility index of the gas, which combustibility index is directly proportional to the Wobbe index. It may also consist of a chromatograph which determines the chemical composition of the gas, from which chemical composition the Wobbe index is calculated. Advantageously, it has a rapid response time. It is in no way excluded to measure said Wobbe index directly by calorimetric methods.

Preferably, in order to carry out the processes of the invention, a combustibility analyzer is used to determine the Wobbe index of the gas.

It will be recalled, for all useful purposes, that said Wobbe index is defined by the ratio of the gross calorific value of the gas to the square root of the density of said gas.

It should be understood here that, in order to carry out the processes of the invention which have been described above, prior work has been accomplished on the flowmeter used, with reference to a given combustible gas family, for which it will be used. We may refer to a prior step of characterizing said flowmeter, of thermal mass technology. Such a method of characterizing such a flowmeter constitutes another subject of the present invention. It is described below.

Said method of characterizing a flowmeter of thermal mass technology—intended to measure volume flow rates of a combustible gas CG of a given family, said flowmeter having been standardized, or standardized and calibrated, beforehand with a reference gas CGo (said reference gas CGo having a composition close to that of said combustible gas CG)—consists in adding to said flowmeter two coefficients a and b, these being calculated as the coefficients of the linear law which approaches the relationship existing between the product of $F_{CG/CGo}$ ($CV_{CG}/CV_{CGo}$) and the Wobbe index $W_{CG}$ of the combustible gas CG, the volume flow rates of which are intended to be measured; which linear law is expressed as:

$$F_{CG/CGo}(CV_{CG}/CV_{CGo}) = aW_{CG} + b( = \frac{\rho_{CG}}{\rho_{CGO}},$$

where $P_{CG}$ is the actual power and $P_{CGo}$ is the apparent power, which powers are calculated by multiplying the flow rates by the calorific values)

with:

$F_{CG/CGo}$: correction factor to be applied to the volume flow rate measurement given by the flowmeter in order to determine the actual volume flow rate of combustible gas CG;

$CV_{CG}/CV_{CGo}$: ratio of the (net or gross) calorific value of the combustible gas CG, the volume flow rate of which is intended to be measured, to the corresponding (net or gross) calorific value of the combustible reference gas CGo.

In order to measure the volume flow rate, said correction factor $F_{CG/CGo}$ may be approximated by the ratio:

$$\frac{\rho_{CGo} CP_{CGo}}{\rho_{CG} CP_{CG}};$$

with:

ρ: density of the gas in question

Cp: heat capacity of the gas in question.

It is not excluded to calculate said correction factor by another method.

The calorific values $CV_{CG}$ and $CV_{CGo}$ are both either net calorific values or gross calorific values.

With regard to said coefficients a and b of the affine function called upon to characterize the flowmeter used, these are advantageously calculated in the following manner:

a) a statistically significant number of compositions representative of the combustible gas are selected: CG, $CG_1$, $CG_2$, ... $CG_n$;

b) for each of said n compositions, the following are calculated or measured:
   the Wobbe index: $W_{CGi}$;
   the same calorific value: $CV_{CGi}$; for example the net calorific value $NCV_{CGi}$ or the gross calorific value $CGV_{CGi}$;
   the correction factor: $F_{CGi/CGo}$;

c) for each of said n compositions, the following product is then calculated:

$$X_{CGi} = F_{CGi/CGo} (CV_{CGi}/CV_{CGo});$$

d) finally, a and b are calculated by a linear regression between the n pairs of data: $(X_{CGi}, W_{CGi})$.

In said calculation, said correction factors may be approximated by the ratio:

$$\frac{\rho_{CGo} CP_{CGo}}{\rho_{CGi} CP_{CGi}}$$

with:

ρ: density of the gas in question

Cp: heat capacity of the gas in question.

The invention also proposes a device for evaluating of the net (or gross) thermal power P of a flow of a combustible gas of composition close to that of a reference gas, comprising:

a flowmeter of thermal mass technology, standardized for said reference gas;

a means for determining the Wobbe index of the gas;

a means for collecting the information given by said flowmeter, and said Wobbe index; and a means for calculating said net (or gross) thermal power P by multiplying the information collected by said flowmeter by the net (or gross) calorific value of said reference gas and by an essentially affine function of the Wobbe index of the gas.

The invention also proposes a device for regulating the net (or gross) thermal power P of a flow of a combustible gas of composition close to that of a reference gas to a value $P_0$, comprising:

the device for evaluating said net (or gross) thermal power P, as defined above; and a means (known per se) for regulating said power P to said value $P_0$.

Said regulating means may act either on the flow rate of the gas or on the composition of said gas (i.e. on its Wobbe index), or jointly on both these parameters. It is therefore capable of including at least one flow-regulating valve and/or at least one means for mixing another gas into said gas.

Advantageously, the regulating device also includes a means for regulating the flow rate of oxidizer employed to the value $Q_0'$ equal to $(1+x)P/K$, where x is the excess oxidizer and where K is a constant which depends on the oxidizer.

Preferably, the device includes a combustibility analyzer for determining the Wobbe index of the gas. Said combustibility analyzer may be placed upstream or downstream of the flowmeter with respect to the direction of the gas flow.

According to another embodiment, the means for determining the Wobbe index of the gas comprises an analyzer for analyzing the chemical composition of said gas.

The invention described above relies on the use of the Wobbe index (W) as characteristic parameter of the combustible gas (CG). It is obvious that the processes and devices described could just as well be based on the use of an equivalent index, such as the combustibility index B. Persons skilled in the art know that said combustibility index (B) is, in the case of natural gas, related to said Wobbe index (W) by the formula:

$$B = \frac{W}{1.16}.$$

In the present description and the appended claims, the term "Wobbe index" therefore covers the actual Wobbe index and the equivalent indices.

Further characteristics and advantages of the invention will appear in the following description of an example, described with reference to the appended figures, in which:

FIG. 1 represents, for thirteen compositions of natural gases and as a function of the Wobbe index of said natural gases, the product:

$$F_{NG/CH_4} (NCV_{NG}/NCV_{CH_4})$$

with $F_{NG/CH_4}$, a correction factor, approximated by the formula $$\frac{\rho_{CH_4} CP_{CH_4}}{\rho_{CG} CP_{CG}}$$

and $NCV_{NG}$, net calorific values, calculated from the composition of the thirteen natural gases used;

FIG. 2 shows, schematically, a distribution system for a combustible gas CG, equipped with means allowing the processes of the invention to be carried out.

Referring more particularly to FIG. 1, the inventor has discovered, in the case of natural gases, a surprising correlation between the Wobbe index of a natural gas—a parameter which can be measured, for example, with a combustibility analyzer—and the ratio of, on the one hand, the actual power at a burner, denoted P, of a flow of said natural gas to, on the other hand, the apparent power, denoted Pc, calculated by multiplying the net calorific value of methane, denoted $NCV_{CH_4}$, by the volume flow rate, denoted $Q_{CH_4}$, of the flow of said natural gas, indicated by a mass flowmeter standardized for methane.

This relationship may be written, by setting $Pc = NCV_{CH_4} Q_{CH_4}$ and by denoting the Wobbe index by "W", as:

$$P/Pc = aW + b$$

with $$a=4.47\times 10^{-2}$$

and $$b=0.3413.$$

This relationship is independent of the natural gas used. Its accuracy is about 0.5%.

This correlation was established for 13 gas compositions, for gases available in France and their mixtures.

This unexpected result makes it possible to use the hot-wire mass flowmeter technology for regulating the power of a combustion plant, and for regulating the combustion ratio, to air or to oxygen, independently of the composition of the natural gas.

The comments below are given with reference to FIG. 2.

The distribution system, shown schematically, feeds two combustion plants 1 and 2 (for example, of the furnaces and burners type) via the main pipe 3 and the secondary pipes 4 and 5.

Said main pipe 3 is fitted, upstream of said secondary pipes 4 and 5, with an apparatus 6 which makes it possible to calculate the Wobbe index W of the gas CG. The value of said Wobbe indices sent to two computers 20 and 20'.

Mounted on the secondary pipe 5 is a flowmeter 7' of thermal mass technology, standardized for a reference gas of composition close to that of said gas CG.

The invention is carried out insofar as the composition of said gas G can vary over time (while still remaining close to that of said reference gas).

The net (or gross) thermal power P' with which the combustion plant 2 is fed is calculated, according to the invention, in the computer 20' from:

the Wobbe index W, determined in the apparatus 6;

the value of the flow rate Q', read on the flowmeter 7';

the net (or gross) calorific value of the reference gas (a constant); and the famous affine function which characterizes the flowmeter 7' used, according to the formula:

$$P'=NCV_{refQ'read}((a'W+b')\ [sic]$$

Mounted in series on the secondary pipe 4 is [sic]:

a flowmeter 7 of thermal mass technology, also standardized for a reference gas and also characterized by coefficients a and b of an affine function; and a member 8 capable of adjusting the feed rate of the gas CG for the combustion plant 1.

This is because, in the case of the feed for said combustion plant 1, provision is made to regulate the net (or gross) thermal power P.

Said net (or gross) thermal power P is calculated, according to the invention, in the computer 20 from:

the Wobbe index W, determined in the apparatus 6;

the flow rate value Q, read on the flowmeter 7;

the net (or gross) calorific value of the reference gas; and the affine function which characterizes said flowmeter 7, according to the formula:

$$P=NCV_{refQread}(aW+b)$$

Said net (or gross) thermal power P is regulated to the value $P_0$ via the regulator 21.

Said regulator 21 controls the member 8 for adjusting the flow rate.

What is claimed is:

1. Process for the evaluation of net (or gross) thermal power P of a flow of a combustible gas CG of composition close to that of a reference gas, said flow of gas passing though a flowmeter of thermal mass technology which is standardized, or standardized and calibrated, for said reference gas, comprising:

a step of collecting flow rate information given by said flowmeter;

a step of determining the Wobbe index of the combustible gas; and a step of calculating said net (or gross) thermal power P by multiplying the collected flow rate information by a net (or gross) calorific value of said reference gas and by an essentially affine function of the Wobbe index of the combustible gas.

2. Process for the regulation of the net (or gross) thermal power P of a flow of a combustible gas CG of composition close to that of a reference gas to a value $P_0$, said flow of gas passing through a flowmeter of thermal mass technology which is standardized, or standardized and calibrated, for said reference gas, comprising:

evaluating said net (or gross) thermal power P, according to the process of claim 1; and regulating said power to said value $P_0$.

3. Process according to claim 1, further comprising a step of regulating a flow rate of oxidizer employed to a value of $Q_0'$ equal to (1+x) P/K, where x represents excess oxidizer and where K is a constant which depends on the oxidizer.

4. Process according to claim 1, wherein the reference gas is methane, propane or butane.

5. Process according to claim 1, wherein when the combustible gas CG used is a natural gas and the reference gas is methane, the essentially affine function is written as:

$$f(W)=aW+b,$$

wherein a is between 0.035 and 0.050 and b is between 0.30 and 0.45.

6. Process according to claim 1, wherein a combustibility analyzer is used for determining the Wobbe index of the combustible gas.

7. Process according to claim 1, wherein the Wobbe index of the combustible gas is determined by a calculation based on results of a chemical analysis of said combustible gas.

8. Device for evaluating net (or gross) thermal power P of a flow of a combustible gas CG of composition close to that of a reference gas, comprising:

a flowmeter of thermal mass technology which is standardized for said reference gas;

a means for determining the Wobbe index of the combustible gas;

a means for collecting flow rate information given by said flowmeter, and said Wobbe index; and a means for calculating said net (or gross) thermal power P by multiplying the flow rate information collected by said flowmeter by a net (or gross) calorific value of said reference gas and by an essentially affine function of the Wobbe index of the combustible gas.

9. Device for regulating the net (or gross) thermal power P of a flow of a combustible gas CG of composition close to that of a reference gas to a value $P_0$, comprising:

a device for evaluating said net (or gross) thermal power P according to claim 8; and a means for regulating said power P to said value $P_0$.

10. Device according to claim 9, further comprising a means for regulating a flow rate of oxidizer used to a value $Q_0'$, equal to $(1+x)P/K$, where x represents excess oxidizer and where K is a constant which depends on the oxidizer.

11. Device according to claim 8, wherein said means for determining the Wobbe index of the combustible gas includes a combustibility analyzer.

12. Device according to claim 8, wherein said means for determining the Wobbe index of the combustible gas comprises an analyzer for analyzing chemical composition of said combustible gas.

13. Process according to claim 2, further comprising a step of regulating a flow rate of oxidizer employed to a value $Q_0'$ equal to $(1+x) P/K$ where x represents excess oxidizer and where K is a constant which depends on the oxidizer.

14. Process according to claim 2, wherein the reference gas is methane, propane or butane.

15. Process according to claim 2, wherein when the combustible gas CG used is a natural gas and the reference gas is methane, the essentially affine function is written as:

$$f(W)=aW+b,$$

wherein a is between 0.035 and 0.050 and b is between 0.30 and 0.45.

16. Process according to claim 2, wherein a combustibility analyzer is used for determining the Wobbe index of the combustible gas.

17. Process according to claim 2, wherein the Wobbe index of the combustible gas is determined by a calculation based on results of a chemical analysis of the combustible gas.

18. Device according to claim 9, wherein said means for determining the Wobbe index of the combustible gas includes a combustibility analyzer.

19. Device according to claim 9, wherein said means for determining the Wobbe index of the combustible gas comprises an analyzer for analyzing chemical composition of said combustible gas.

* * * * *